US00PP25785P2

(12) United States Plant Patent
Jamieson

(10) Patent No.: US PP25,785 P2
(45) Date of Patent: Aug. 4, 2015

(54) ***AGAPANTHUS* PLANT NAMED 'CROFT'S PEARL'**

(50) Latin Name: *Agapanthus praecox*
Varietal Denomination: Croft's Pearl

(71) Applicant: Richard Jamieson, Kirstenhof (ZA)

(72) Inventor: Richard Jamieson, Kirstenhof (ZA)

(73) Assignee: THE PINK GERANIUM NURSERY, Elsenburg (ZA)

( * ) Notice: Subject to any disclaimer, the term of this patent is extended or adjusted under 35 U.S.C. 154(b) by 56 days.

(21) Appl. No.: 13/999,098

(22) Filed: Jan. 13, 2014

(51) Int. Cl.
*A01H 5/02* (2006.01)

(52) U.S. Cl.
USPC ..... Plt./398

(58) Field of Classification Search
USPC ..... Plt./398
CPC ..... A01H 5/025; A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Agapanthus* named 'Croft's Pearl', characterized by its metallic blue flower buds that remain in the bud stage and do not open, its sterile flowers, and its long lasting cut flowers.

2 Drawing Sheets

Botanical classification: *Agapanthus praecox*.
Varietal denomination: 'Croft's Pearl'.

BACKGROUND OF THE INVENTION

The present invention relates to a new and distinct cultivar of *Agapanthus praecox* and will be referred to hereafter by its cultivar name, 'Croft's Pearl'. 'Croft's Pearl' represents a new perennial herb grown for landscape and cut flower use.

The new *Agapanthus* originated as the result of an on going breeding program in Cape Town, Republic of South Africa. The goal of the breeding program was to produce a sterile cultivar of *Agapanthus* with full and rounded flower heads.

'Croft's Pearl' originated as a seedling that arose from seed planted from open pollination of an unnamed plant of *Agapanthus praecox* from the Inventor's breeding program. The male parent is unknown. The new *Agapanthus* was selected as a single unique plant in 2004.

Asexual propagation of the new cultivar was first accomplished by in vitro propagation under the direction of the Inventor in December of 2005 in Cape Town, Republic of South Africa. Asexual propagation by division and tissue culture has determined that the characteristics of this cultivar are stable and are reproduced true to type in successive generations.

SUMMARY OF THE INVENTION

The following traits have been repeatedly observed and represent the characteristics of the new cultivar. The characteristics in combination distinguish 'Croft's Pearl' as a distinct cultivar of *Agapanthus*.

1. 'Croft's Pearl' exhibits metallic blue flower buds that remain in the bud stage and do not open.
2. 'Croft's Pearl' exhibits sterile flowers.
3. 'Croft's Pearl' produces long lasting cut flowers.

The female parent differs from 'Croft's Pearl' in having flowers that are fertile, flower buds that open, and in having cut flowers that are not as long lasting in a vase. 'Croft's Pearl' can be compared to the cultivars 'Peter Pan' (not patented) and 'Snowball' (not patented). 'Peter Pan' is similar to 'Croft's Pearl' in being evergreen and in having blue flowers, but differs from 'Croft's Pearl' in having fertile flowers that open, in being shorter in plant height, and in having flower heads that are less full. 'Snowball' is similar to 'Croft's Pearl' in having full flower heads and in being evergreen. 'Snowball' differs from 'Croft's Pearl' in having fertile white flowers and a shorter plant height.

BRIEF DESCRIPTION OF THE DRAWINGS

The accompanying colored photographs illustrate the overall appearance and distinct characteristics of the new *Agapanthus*. The photographs were taken of a three year-old plant of 'Croft's Pearl' as field grown outdoors in Cape Town, Republic of South Africa.

The photograph in FIG. 1 provides a close-up view of an inflorescence of 'Croft's Pearl'.

Figure 1:
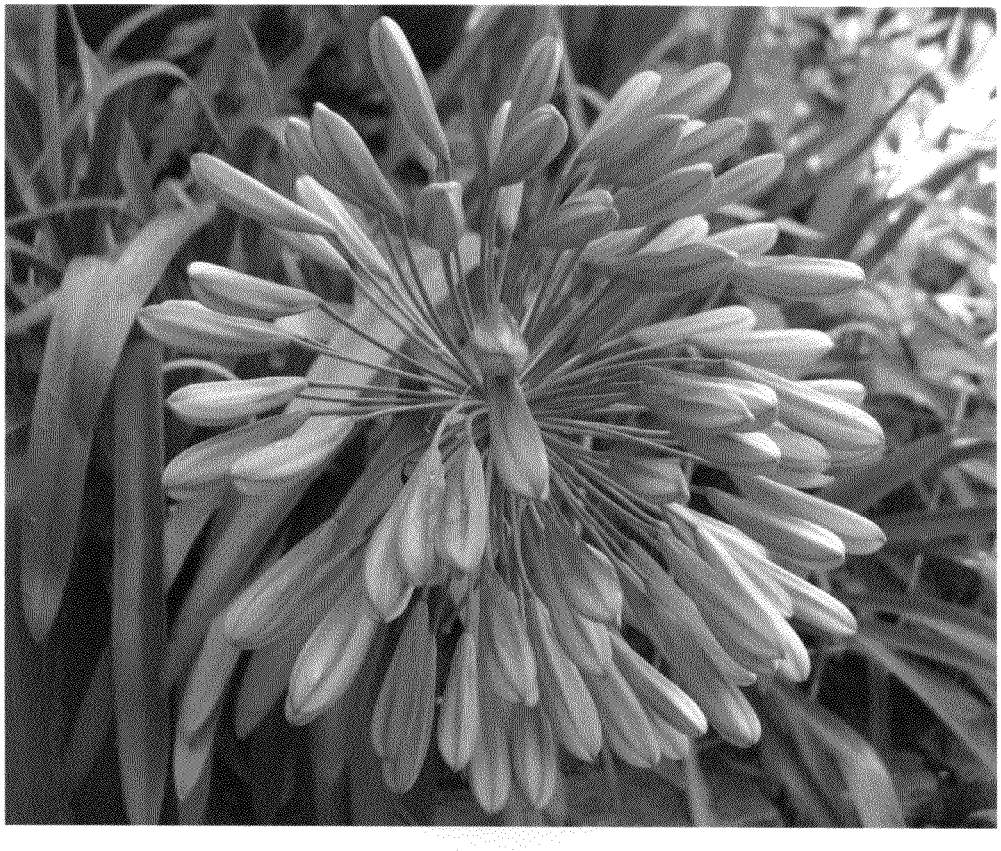
Figure 2:
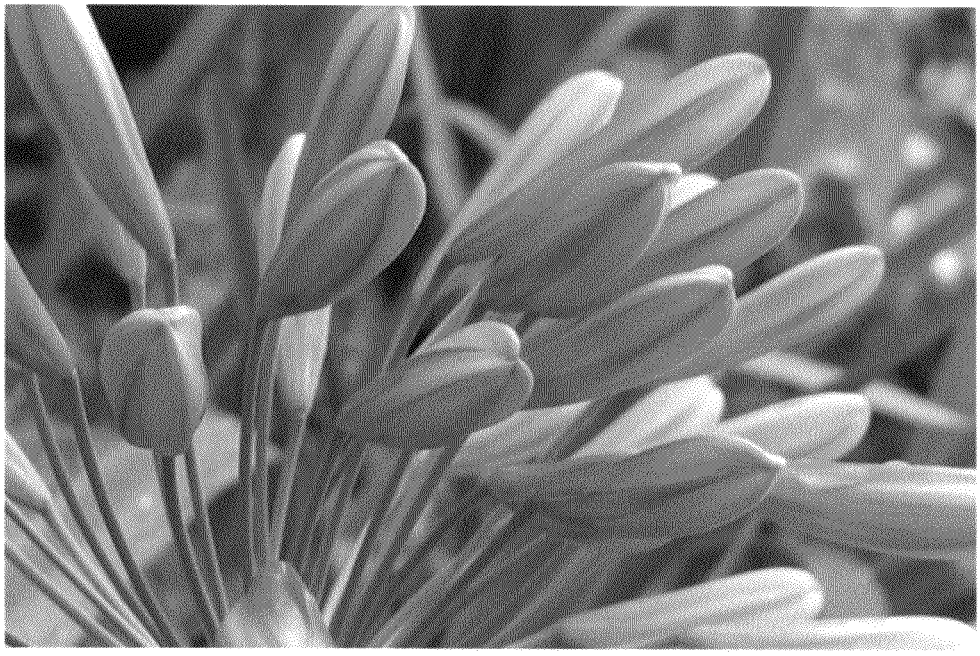

The photograph in FIG. 2 provides a close-up view of the flower buds of 'Croft's Pearl'.

The colors in the photographs are as close as possible with the photographic and printing technology utilized and color values cited in the detailed botanical description accurately describe the colors of the new *Agapanthus*.

DETAILED BOTANICAL DESCRIPTION

The general observations and descriptions describe plants about two year-old in age as grown outdoors under field conditions in Cape Town, Republic of South Africa. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—4 to 6 weeks in mid summer in Cape Town, Republic of South Africa.

*Plant type*.—Evergreen perennial herb.
*Plant habit*.—Upright and slightly cascading.
*Height*.—Reaches a height of about 80 cm in bloom.
*Cold hardiness*.—At least to U.S.D.A. Zone 8.
*Diseases and pests*.—No susceptibility or resistance to diseases or pests has been observed.
*Root description*.—Fleshy main roots and fibrous secondary roots.
*Propagation*.—Tissue culture and division.
*Growth rate*.—Moderately vigorous.

Foliage description:

*Leaf shape*.—Linear.
*Leaf division*.—Simple.
*Leaf base*.—Cuneate.
*Leaf arrangement*.—2-ranked, in rosette.
*Leaf apex*.—Acute.
*Leaf aspect*.—Emerging leaves erect, then cascade.
*Leaf venation*.—Parallel, color matches leaf coloration.
*Leaf margins*.—Entire.
*Leaf size*.—Average of 40 cm in length and 2.3 cm in width.
*Leaf surface*.—Glabrous, slightly glossy.
*Leaf substance*.—Thick and leathery, moderate to high durability to stress.
*Leaf number*.—Average of 12 per rosette.
*Leaf color*.—Young leaves, upper surface; Yellow-Green 146B young leaves, lower surface; Yellow-Green 146C, mature leaves, upper surface; Yellow-Green 146B and White 157B near base, mature leaves, lower surface; Yellow-Green 146C and White 157B near base.
*Leaf attachment*.—Sessile to crown.

Flower description:

*Inflorescence type*.—Simple umbel.
*Flower fragrance*.—None.
*Flower type*.—Closed buds.
*Flower number*.—Full flower heads; an average of about 65 flowers per umbel, one umbel per peduncle and one peduncle per rosette.
*Inflorescence size*.—Average of 6 cm in depth and 14 cm in diameter.
*Flower size*.—About 3.5 cm in depth and 0.75 cm in width.
*Lastingness of inflorescence*.—About 40 days.
*Longevity as a cut flower*.—About 10 days.
*Flower aspect*.—Held outward to slightly downward from pedicel.
*Peduncle*.—Strong, somewhat flattened, held erect, average of 55 cm in length and 6 cm in width at distal region and 7 mm in width at proximal region, surface is glabrous, color Yellow-Green 144B.
*Pedicels*.—Strong, average of 2.9 cm in length and 1 mm in width, held erect to outward, color Yellow-Green147B, surface is glabrous.
*Flower buds*.—Obovate in shape, average of 3.5 cm in length and 0.75 mm in width, color Violet Blue 89D.
*Tepals*.—6, fused and do not open, narrow obovate in shape, entire margin, glabrous texture, acute apex, base fused, average of 3.5 cm in length and 0.75 mm in width, color when young; Violet Blue 91B, color mature; Violet Blue 90D.

Reproductive organs:

*Gynoecium*.—1 pistil, average of 1.6 cm in length, stigma is narrow clavate in shape and Violet Blue 91B in color, style is about 1.9 cm in length and Violet-Blue 91B in color, ovary is Yellow-Green 150B in color.
*Androecium*.—6 stamens, anthers are dorsified, oblong in shape, average of 2 mm in length, and Grey-Orange 165B in color, filament is 2.2 cm in length, pollen is low in quantity and Violet-Blue 91B in color.
*Fruit/seed*.—Have been observed to be sterile (flowers non opening).

It is claimed:

1. A new and distinct cultivar of *Agapanthus* plant named 'Croft's Pearl' as herein illustrated and described.

* * * * *